United States Patent [19]

Meinke et al.

[11] Patent Number: 5,162,363
[45] Date of Patent: Nov. 10, 1992

[54] 23-NOR-23-THIA AVERMECTIN ANALOGS ARE ACTIVE ANTHELMINTIC AGENTS

[75] Inventors: Peter T. Meinke, New York, N.Y.; Helmut Mrozik, Matawan, N.J.

[73] Assignee: Merck & Co., Inc., Rahway, N.J.

[21] Appl. No.: 853,451

[22] Filed: Mar. 18, 1992

[51] Int. Cl.$^5$ ............... A61K 31/39; C07D 411/14
[52] U.S. Cl. ........................... 514/433; 549/14; 514/30; 536/7.1
[58] Field of Search ............ 549/14, 264; 514/433, 514/450, 30; 536/7.1

[56] References Cited

U.S. PATENT DOCUMENTS

| Re. 32,006 | 10/1985 | Chabala et al. | 549/264 |
|---|---|---|---|
| Re. 32,034 | 11/1985 | Chabala et al. | 549/264 |
| 4,199,569 | 4/1980 | Chabala et al. | 514/30 |
| 4,200,581 | 4/1980 | Fisher et al. | 549/264 |
| 4,201,861 | 5/1980 | Mrozik et al. | 549/264 |
| 4,310,519 | 1/1982 | Albers-Schonberg et al. | 549/264 |
| 4,427,663 | 4/1980 | Fuchs et al. | 549/264 |
| 4,895,837 | 1/1990 | Mrozik et al. | 549/264 |
| 4,906,619 | 3/1990 | Eskola et al. | 549/264 |

*Primary Examiner*—Richard L. Raymond
*Assistant Examiner*—Mark W. Russell
*Attorney, Agent, or Firm*—David L. Rose; Joseph F. DiPrima

[57] ABSTRACT

Avermectin analogs are prepared where the 23-position ring carbon atom is deleted and replaced by a sulfur atom. The compounds are prepared by opening the outer spiroketal ring to gain access to the 23-position atom, substituting the ring-opened compounds with a substituent containing the sulfur atom in the appropriate position and closing the ring to prepare the desired compounds. The compounds are potent anthelmintic agents and methods and compositions including such 23-nor-23-thia compounds are also disclosed.

8 Claims, No Drawings

23-NOR-23-THIA AVERMECTIN ANALOGS ARE ACTIVE ANTHELMINTIC AGENTS

BACKGROUND OF THE INVENTION

Avermectin compounds have been known for some time as potent anthelmintic agents and substantial research has been carried out preparing various substituted variations of such compounds. Some of the avermectin compounds have become commercially available as potent broad-spectrum anthelmintic and antiparasitic agents in animal health and agriculture. See US 4310519 to Albers-Schonberg et al and 4199569 to Chabala et al. Applicants are not aware of any avermectin compounds where the 23-ring carbon has been replaced by a heteroatom.

SUMMARY OF THE INVENTION

This invention is concerned with the preparation of 23-nor-23-thia avermectin compounds that are prepared from avermectin natural products or derivatives thereof in a series of reactions that first opens the avermectin spiroketal ring containing the C23 ring carbon atom. The 23-carbon atom is then replaced by a sulfur containing group which may also have additional substituents thereon and the compound is then ring closed to prepared the desired compounds. The 23-nor-23-thia compounds are highly effective anthelmintic and antiparasitic agents in animal health and agriculture.

DESCRIPTION OF THE INVENTION

The compounds of the instant invention are best realized in the following structural formula.

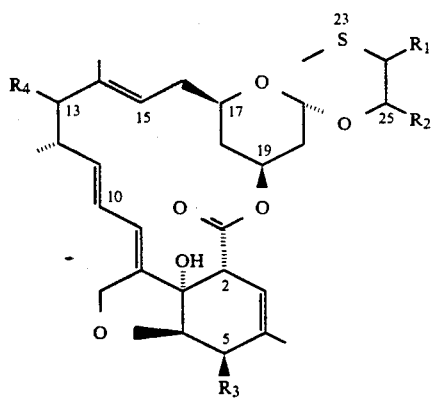

where
$R_1$ and $R_2$ are independently hydrogen, $C_1-C_{10}$ alkyl, $C_2-C_{10}$ alkenyl, $C_2-C_{10}$ alkynyl, $C_1-C_{10}$ alkoxy $C_1-C_{10}$ alkyl or $C_1-C_{10}$ alkylthio $C_1-C_{10}$ alkyl group; a $C_3-C_8$ cycloalkyl or $C_5-C_8$ cycloalkenyl group, either of which may optionally be substituted by methylene or from 1 to 3 of $C_1-C_4$ alkyl groups or halo atoms; phenyl, phenoxy, $C_{1-10}$ alkyl phenyl, $C_2-C_{10}$ alkenyl phenyl, $C_2-C_{10}$ alkynyl phenyl, substituted $C_1-C_{10}$ alkyl wherein the substituents independently are 1 to 3 of $C_1-C_5$ alkyl, $C_3-C_8$ cycloalkyl or substituted $C_1-C_{10}$ alkyl wherein the substituents are independently 1 to 3 of hydroxy, halogen, cyano, $C_1-C_5$ alkyl thio, $C_1-C_5$ alkyl sulfinyl, $C_1-C_5$ alkyl sulfonyl, amino, $C_1-C_5$ mono or dialkyl amino, $C_1-C_5$ alkanoyl amino or $C_1-C_5$ alkanoylthio; or a 3 to 6 membered oxygen or sulfur containing heterocyclic ring which may be saturated or fully or partly unsaturated and which may optionally be substituted independently by 1 to 3 of $C_1-C_5$ alkyl or halogen; or
$R_3$ is hydroxy, $C_1-C_5$-alkoxy, hydroximino or —O—$C_1$–$C_5$ alkyl-hydroximino;
$R_4$ is hydrogen, halogen, hydroxy, $C_1-C_5$ alkanoyloxy, ($C_1-C_5$-alkoxy)$_n$ where n is 1–4,

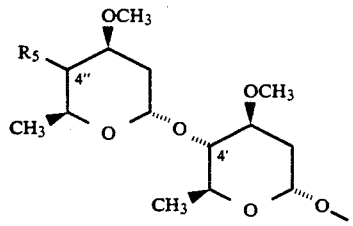

or

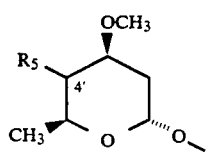

where $R_5$ is hydroxy, oxo, ($C_1-C_5$ alkyl)$_m$ amino, $C_1-C_5$ alkanoyl amino, ($C_1-C_5$ alkyl) ($C_1-C_5$ alkanoyl) amino, $C_1-C_5$ alkyl-S(O)$_m$, hydroxy substituted $C_1-C_5$ alkyl S(O)$_m$, where m is 0, 1 or 2 or ($C_1-C_5$-alkoxy)$_n$ where n=1–4.

In the foregoing structural formula and throughout the instant specification the alkyl, groups are intended to be of either a straight or branched configuration. The ($C_1-C_5$ alkoxy)$_n$ is intended to include alkoxy and polyalkoxy groups of either a straight or branched configuration and where the polyalkoxy group can independently vary as to carbon atom content and configuration.

Preferred compounds of the instant invention are realized in the foregoing structural formula wherein:
$R_1$ and $R_2$ are independently hydrogen, $C_1-C_5$ alkyl, $C_2-C_5$ alkenyl, $C_1-C_5$ alkoxy, a $C_5-C_6$ cycloalkyl or $C_5-C_6$ cycloalkenyl group, either of which may optionally be substituted by methylene or from 1 to 3 of $C_1-C_4$ alkyl groups; phenyl, phenoxy, $C_{1-5}$ alkyl phenyl, $C_2-C_5$ alkenyl phenyl, substituted $C_1-C_5$ alkyl wherein the substituents independently are 1 to 3 of $C_1-C_3$ alkyl, $C_1-C_3$ alkyl thio, $C_1-C_3$ alkyl sulfinyl, $C_1-C_3$ alkyl sulfonyl, or a 5 to 6 membered oxygen or sulfur containing heterocyclic ring which may be saturated or fully or partly unsaturated; or
$R_3$ is hydroxy, $C_1-C_3$-alkoxy, $C_1-C_3$-alkanoyloxy hydroximino or —O—$C_1-C_5$ alkyl-hydroximino;
$R_4$ is hydrogen, halogen, hydroxy, $C_1-C_3$-alkanoyloxy, ($C_1-C_3$ alkoxy), where n is 1–2,

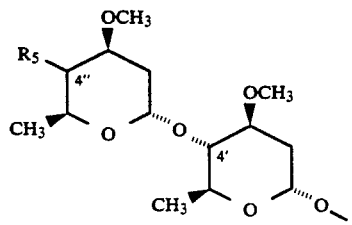

-continued
or

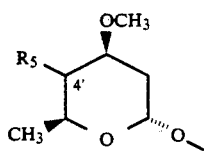

where $R_5$ is hydroxy, $C_1-C_3$ alkyl amino, $C_1-C_3$ alkanoyl amino, $(C_1-C_3$ alkyl) $(C_1-C_3$ alkanoyl) amino, $C_1-C_3$ alkyl-$S(O)_m$, hydroxy substituted $C_1-C_3$ alkyl $S(O)_m$, where m is 0, 1 or 2 or $(C_1-C_3$-alkoxy)$_n$ where n=1–4.

More preferred compounds of the instant invention are realized in the foregoing structure where:

$R_1$ is hydrogen, $C_1-C_4$-alkyl;

$R_2$ is hydrogen, $C_1-C_5$ alkyl, $C_2-C_5$ alkenyl, $C_1-C_5$ alkoxy, a $C_5-C_6$ cycloalkyl or $C_5-C_6$ cycloalkenyl group, phenyl, substituted $C_1-C_5$ alkyl wherein the substituents independently are 1 to 3 of $C_1-C_3$ alkyl; or $R_3$ is hydroxy, hydroximino or $-O-C_1-C_2$ alkylhydroximino;

$R_4$ is hydrogen, halogen, hydroxy, $C_1-C_2$-alkanoyloxy, $(C_1-C_3$ alkoxy)$_n$ where n is 1–2,

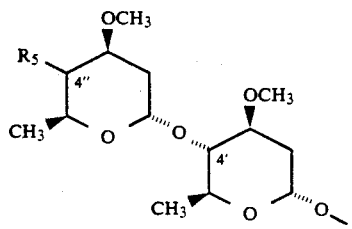

or

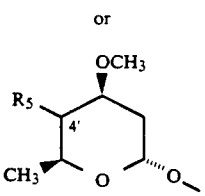

where $R_5$ is hydroxy, $C_1-C_2$ alkyl amino, $C_1-C_2$ alkanoyl amino, $(C_1-C_2$ alkyl) $(C_1-C_2$ alkanoyl) amino, $C_1-C_2$ alkyl-$S(O)_m$, hydroxy substituted $C_1-C_2$ alkyl $S(O)_m$, where m is 0, 1 or 2.

Additional preferred compounds of this invention are:

23-nor-23-thia-24-desmethyl-25-des(2-butyl) ivermectin B1;
23-nor-23-thia-24-desmethyl-25-des(2-butyl)-25-methyl ivermectin B1;
23-nor-23-thia-24-desmethyl-25-des(2-butyl)-25-ethyl ivermectin B1;
23-nor-23-thia-24-desmethyl-25-des(2-butyl)-25-isopropyl ivermectin B1;
23-nor-23-thia-24-desmethyl-25-des(2-butyl)-25-tert-butyl ivermectin B1;
23-nor-23-thia-24-desmethyl-25-des(2-butyl)-25-sec-butyl ivermectin B1;
23-nor-23-thia-24-desmethyl-25-des(2-butyl)-25-[2-(4-methylpent-2-enyl)] ivermectin B1;
23-nor-23-thia-24-desmethyl-25-des(2-butyl)-25-cyclohexyl ivermectin B1;
23-nor-23-thia-24-desmethyl-25-des(2-butyl)-25-phenyl ivermectin B1;
23-nor-23-thia-24-desmethyl-25-des(2-butyl)-25-(4-fluoro)phenyl ivermectin B1;
23-nor-23-thia-24-desmethyl-25-des(2-butyl)-25-(4-methoxy)phenyl ivermectin B1;
23-nor-23-sulfinyl-24-desmethyl-25-des(2-butyl) ivermectin B1;
23-nor-23-sulfinyl-24-desmethyl-25-des(2-butyl)-25-methyl ivermectin B1;
23-nor-23-sulfinyl-24-desmethyl-25-des(2-butyl)-25-isopropyl ivermectin B1;
23-nor-23-sulfinyl-24-desmethyl-25-des(2-butyl)-25-tert-butyl ivermectin B1;
23-nor-23-sulfinyl-24-desmethyl-25-des(2-butyl)-25-cyclohexyl ivermectin B1;
23-nor-23-sulfinyl-24-desmethyl-25-des(2-butyl)-25-sec-butyl ivermectin B1;
23-nor-23-sulfinyl-24-desmethyl-25-des(2-butyl)-25-ethyl ivermectin B1;
23-nor-23-sulfinyl-24-desmethyl-25-des(2-butyl)-25-[2-(4-methylpent-2-enyl)] ivermectin B1;
23-nor-23-sulfinyl-24-desmethyl-25-des(2-butyl)-25-phenyl ivermectin B1;
23-nor-23-sulfonyl-24-desmethyl-25-des(2-butyl) ivermectin B1;
23-nor-23-sulfonyl-24-desmethyl-25-des(2-butyl)-25-methyl ivermectin B1;
23-nor-23-sulfonyl-24-desmethyl-25-des(2-butyl)-25-isopropyl ivermectin B1;
23-nor-23-sulfonyl-24-desmethyl-25-des(2-butyl)-25-tert-butyl ivermectin B1;
23-nor-23-sulfonyl-24-desmethyl-25-des(2-butyl)-25-cyclohexyl ivermectin B1;
23-nor-23-sulfonyl-24-desmethyl-25-des(2-butyl)-25-sec-butyl ivermectin B1;
23-nor-23-sulfonyl-24-desmethyl-25-des(2-butyl)-25-ethyl ivermectin B1;
23-nor-23-sulfonyl-24-desmethyl-25des(2-butyl)-25-[2-(4-methylpent-2-enyl)] ivermectin B1;
23-nor-23-sulfonyl-24-desmethyl-25-des(2-butyl)-25-phenyl ivermectin B1;
23-nor-23-sulfonyl-24-desmethyl-25-des(2-butyl)-25-(4-fluoro)phenyl ivermectin B1;
23-nor-23-thia-24-desmethyl-25-des(2-butyl)-4"-deoxy-4"-epi-amino-25-isopropyl ivermectin B1;
23-nor-23-sulfonyl-24-desmethyl-25-des(2-butyl)-4"-deoxy-4"-epi-acetylamino-25-tert-butyl ivermectin B1;
23-nor-23-sulfinyl-24-desmethyl-25-des(2-butyl)-4"-deoxy-4"-epi-acetyl(methyl)amino-25-cyclohexyl ivermectin B1;
23-nor-23-thia-24-desmethyl-25-des(2-butyl)-5-deoxy-5-ketoxime-25-sec-butyl ivermectin B1;
23-nor-23-sulfonyl-24-desmethyl-25-des(2-butyl)-25-ethyl ivermectin B1 monosaccharide;
23-nor-23-thia-24-desmethyl-25-des(2-butyl)-25-[2-(4-methylpent-2-enyl)] ivermectin B1 aglycone;
23-nor-23-sulfonyl-24-desmethyl-25-des(2-butyl)-13-O-methoxymethyl-25-phenyl ivermectin B1 aglycone;
23-nor-23-sulfinyl-24-desmethyl-25-des(2-butyl)-13-deoxy-13-fluoro-25-(4-fluoro)phenyl ivermectin B1;
23-nor-23-thia-24-desmethyl-25-des(2-butyl)-13-O-methoxyethoxymethyl-25-isopropyl ivermectin B1 aglycone;

23-nor-23-sulfonyl-24-desmethyl-25-des(2-butyl)-13-deoxy-13-chloro-25-tert-butyl ivermectin B1 aglycone;

23-nor-23-thia-24-desmethyl-25-des(2-butyl)-13-deoxy-25-cyclohexyl ivermectin B1 aglycone;

23-nor-23-sulfonyl-24-desmethyl-25-des(2-butyl)-4''-deoxy-4''-epi-(2-acetylaminoethyl)thio-25-sec-butyl ivermectin B1;

23-nor-23-sulfonyl-24-desmethyl-25-des(2-butyl)-4''-deoxy-4''-epi-(2-acetylaminoethyl)sulfonyl-25-tert-butyl ivermectin B1.

The compounds of the instant invention are prepared in a series of reactions beginning with the natural product avermectins or derivatives thereof. The reaction sequence used to prepare the instant compounds is shown in Reaction Scheme 1. For clarity and simplicity, the Reaction Scheme shows only carbon atoms numbered 17 and higher.

-continued
REACTION SCHEME I

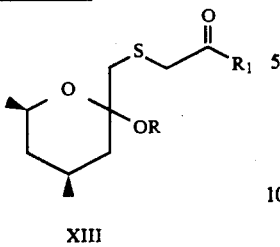

XIII

The critical intermediate III is prepared in six steps from avermectin starting material I (for purposes of example shown as avermectin B$_2$a) with the 6,6-spiroketal ring system and the appropriate substituents at the remainder of the molecule or with a substitution pattern from which the substituent groups at the remainder of the molecule can be prepared after the synthesis of the instant compounds.

Compound I, suitably protected at the hydroxy groups, is reacted with an oxidizing agent such as oxalyl chloride in DMSO in the presence of at least 2 equivalents of a base to react with the HCl liberated during the course of the reaction. The reaction is carried out initially in the cold at temperatures less than 0° C. and preferably less than −50° C. and is generally complete in from 1 to 10 hours affording the 23-keto compound.

In the next step the 23-keto compound is reacted with an alkali metal bis(trimethylsilyl)amide to form the enol ether with a 22,23-double bond. The reaction is carried out in the cold at a temperature less than 0° C. and preferably less than −50° C. under an inert atmosphere in a non-reactive solvent such as a hydrocarbon, preferably an alkane or other nonpolar solvents such as tetrahydrofuran that will remain liquid at reaction temperatures. Generally mixtures of C$_6$ to C$_9$ alkanes, preferably hexanes, are used. The reaction is generally complete in from 1 to 10 hours. The choice of the base in this reaction is very important since it is well known that strong bases readily epimerize the 2-position of the avermectin molecule and rearrange the 3,4-double bond to give analogs of low biological potency. It was found that from a selection of numerous bases, an alkali metal bis(trimethylsilyl)amide is capable of forming the desired silyl enol ether without any further side reactions.

In the next step the 22,23-double bond is epoxidized with a mild oxidizing agent, preferably a peroxy acid such as meta-chloroperbenzoic acid. The reaction is carried out in an inert solvent such as a chlorinated hydrocarbon such as chloroform or methylene chloride and the like at a temperature of from 0° to 50° C. and is generally complete in about 10 minutes to 2 hours.

In the final step of the reaction of compound I to prepare compound II the 22,23-epoxide is treated with acidic methanol to hydrolize the epoxide and form compound II. The reaction is carried out at about room temperature and is generally complete in from 5 minutes to 2 hours.

In the foregoing series of reactions the intermediates may be isolated and purified, however it has not been found necessary to do so and if desired, the reactions may be carried out in a single reaction vessel, only isolating compound II at the conclusion of the series of four reaction steps.

Compound II is then cleaved to form the critical intermediate III. Compound II is treated with lead tetraacetate which cleaves the 22,23-bond affording critical intermediate III.

Compound III may be transketallized in a protic solvent, preferably methanol or isopropyl alcohol, using an organic acid such as pyridinium p-toluenesulfonate. In methanol, transketallization of III replaces the large side chain containing atoms 23-25 with a smaller methoxy group, thereby forming methoxy-aldehyde IV. The aldehyde function of IV may be selectively reduced with hydride reagents to produce an intermediate alcohol which is converted into the trifluoromethanesulfonate Va. The aldehyde function of aldehyde-ester III is converted into an alcohol under identical conditions and subsequently sulfonylated to form trifluoromethanesulfonate Vb. Triflates Va and Vb differ only in the group R (methoxy for the former while the latter contains the original side chain). The reduction of the aldehyde group of III or IV was best accomplished using sodium borohydride in methanol at 0° C. Other reducing reagents such as LiAlH$_4$, LiBH$_4$, diisobutylaluminum hydride and the like in aprotic solvents such as THF or ether at low temperature also were satisfactory. Sulfonylation reactions were best performed using amine bases such as pyridine, 4-dimethylaminopyridine or diisopropylethylamine in inert chlorinated solvents, preferably methylene chloride or chloroform at 0° C.

Treatment of either Va or Vb with an appropriately substituted sulfur nucleophile in a polar aprotic solvent in the presence of base yields sulfide VI. The displacement reaction was facilitated by the addition of 18-crown-6, generally resulting in shorter reaction times. Alcohol VI was cyclized in an inert chlorinated solvent, preferably methylene chloride using a mixture of pyridinium p-toluenesulfonate and p-toluenesulfonic acid at room temperature to formation the new 23-nor-23-thia avermectin derivatives VII. Cyclization of VI to VII also could be run successfully in methanol using p-toluensulfonic acid, however these conditions entailed heating the reaction to 40° C.

Sulfide VII was oxidized in inert solvents, such as methylene chloride or chloroform, to form sulfinyl analogs VIII and sulfonyl analogs IX. The oxidant of choice was meta-perbenzoic acid. The oxidation of sulfide VII could also be performed using oxidants such as sodium metaperiodate in methanol:water (1:1) or periodic acid in methylene chloride or chloroform. The oxidations could be run to generate the sulfoxides or sulfones selectively or produce mixtures of both if so desired.

Additional strategies for the preparation of 23-nor-23-thia-modified avermectins VII were developed. Triflate Va or Vb could be treated with potassium thioacetate in dimethylformamide at room temperature to yield the corresponding acetylthio derivative. The acetyl function could be removed using hydride nucleophiles in ethereal solvents, such as ether or THF, to generate thiol XII. Appropriate reducing agents include, but are not restricted to LiAlH$_4$, LiBH$_4$ and diisobutylaluminum hydride. Reaction of thiol XII with an appropriate alpha-halo ketone allowed for selective formation of XIII. The ketone of compound XIII may be reduced with a variety of hydride sources to form either racemic or optically pure VI. These hydride sources include, but are not restricted to, NaBH$_4$, LiAlH$_4$, LiBH$_4$, diisobutylaluminum hydride and oxazaborolidines. As before, alcohol VI may be cyclized under acidic conditions to generate sulfide VII.

An alternative method for the production of sulfide VII is disclosed as follows. Alcohol VI, where $R_1=R_2=H$, may be oxidized to its corresponding aldehyde (X). Preferred oxidants include the Dess-Martin periodinane, pyridinium dichromate, pyridinium chlorochromate and methyl sulfoxide/oxalyl chloride. Aldehyde X reacts readily with aromatic and aliphatic Grignard reagents (RMgBr) or lithium reagents (RLi) to produce VI. As before, alcohol VI may be cyclized under acidic conditions to generate sulfide VII.

Deprotection to remove the silyl protecting groups of sulfides VII is best accomplished using HF.pyridine in THF.

Treatment of compounds VII, VIII or IX with 1% sulfuric acid in methanol at room temperature for twelve hours allows for the preparation of the aglycones in deprotected form. If this reaction is run for four hours in isopropanol using 1% sulfuric acid, formation of the monosaccharides occurs.

Deprotection is best achieved using HF.pyridine in THF at room temperature for 12–48 hours. Deprotection of Va/b to yield VIIa/b under the identical conditions also proceeds readily.

Separation of stereoisomers, if present, is possible while at the VII and deprotected stages. The isomers may be separated, if desired, by thin layer preparative chromatography, flash chromatography or high pressure liquid chromatography (normal or reverse phase). Isomer separation at these various stages is dictated primarily by ease of separation at any given point.

The foregoing series of reactions is carried out using protecting groups on the reactive functions, such as hydroxy groups, on the avermectin molecule. Following the completion of the reaction sequence, the protecting groups may be removed to afford the unprotected final product. The isomers can be readily separated from each other prior to the removal of the protecting groups using chromatographic techniques, such as column chromatography. If the protecting groups are removed, the separation of the isomer is still readily accomplished chromatographically using thin layer or preparative layer chromatography or reverse phase high pressure liquid chromatography. The mixtures of stereoisomers as well as the isolated stereoisomers have been found to have substantial activity as antiparastic or insecticidal products.

Some additional substituents can be prepared on the instant compound using techniques known to those skilled in the art, such as the introduction of alkylthio or substituted alkylthio substitutents at the 4'- and 4"-positions and the oxidized derivatives thereof. The substituents can be synthesized either prior to the preparation of the 23-nor-23-thia ring system or after the 23-nor-23-thia ring system is prepared. However, to avoid undesired side-reactions, in particular where the alkylthio group contains reactive substituents, it is often preferred to prepare the 4'- or 4"-alkylthio substituent after the reactions for the preparation of the 23-nor-23-thia ring system have been completed.

The preparation of the 4'- and 4"-alkylthio compounds of this invention is best accomplished when the avermectin starting materials are protected at the 5-hydroxy position to avoid substitution at this position. With this position protected, the reactions may be carried out at the 4"- or 4'-positions without affecting the remainder of the molecule. The 5-hydroxy group is protected by a tert.-butyldimethylsilyl group before displacement at the 4"- or 4'-hydroxyl group has occurred. The 7-hydroxy group is very unreactive and need not be protected.

The preparation of the 4'- and 4"-alkylthio compounds requires that the avermectin starting materials are converted into derivatives with good leaving groups at the 4"- or 4'-position, preferably halo- or alkyl-substituted sulfonyl groups, more preferably trifluoromethanesulfonyl- or iodo-groups. Subsequently, these leaving groups are displaced by sulfur-containing nucleophiles to obtain the desired 4"-deoxy-4"-alkylthio avermectin derivatives (which also may be modified further).

The 4"- or 4'-alkyl substituted sulfonyl intermediate is prepared from the 5-position protected avermectin using the appropriate sulfonic anhydride or the appropriate sulfonyl chloride in an inert solvent such as a chlorinated hydrocarbon, tetrahydrofuran (THF), or ether, preferably methylene chloride, in the presence of base at $-15°$ to $10°$ C. over a period of 15 minutes to 1 hour. The 4"- or 4'-alkyl substituted sulfonyl compound may be isolated using techniques known to those skilled in the art. Then the 4"- or 4'-sulfonylavermectin is substituted at the 4"- or 4'-position by sulfur-containing nucleophiles. The reaction is carried out at or near at room temperature in an inert solvent such as dimethylformamide (DMF), dimethylsulfoxide (DMSO), THF, chlorinated hydrocarbons, or ether, preferably DMF, with the desired thiol nucleophile, either the metallic thiol or a thiol with a base such as potassium carbonate at $0°$ to $25°$ C. over a period of 1 to 4 hours. It has been found useful to include in the reaction mixture a small quantity of crown ethers such as 18-crown-6 (1,4,7,10,13,16-hexaoxacyclooctadecane). The presence of the crown ether facilitates the reaction and generally significantly reduces the duration of the reaction. The products are isolated using known techniques.

There are two possible epimers at the 4"- or 4'-position; one with the stereochemistry exactly as in the natural avermectins with an equatorial (or $\alpha$) substituent and one with the axial (or $\beta$) configuration. The latter is called 4"- or 4'-epi. The reaction with strong nucleophiles results predominantly in the product with the inverted configuration. The reaction with hard nucleophiles usually gives both compounds, which are separable, but since both possess high biological activities, they need not be separated. Both epimers are considered part of this invention, either separate or in a mixture.

Nucleophilic substitution of the leaving group can be also accomplished by iodine, by adding a halogen salt to a stirred solution of the avermectin substituted with a good leaving group at the 4"-position in DMF, DMSO, THF or a chlorinated hydrocarbon and allowing the reaction to stir at room temperature from 1 to 6 hours. The product is isolated using known techniques. The 4"-halogen atom can, in turn, be displaced by other nucleophiles, including other sulfur-containing nucleophiles.

In addition, the sulfur-containing 4"-substituent can be further modified. Oxidation of the 4"-sulfur in an unreactive solvent with an oxidizing agent such as m-chloroperbenzoic acid at $-15°$ to $25°$ C. for a period of 30 minutes to 2 hours gives the sulfoxide and the sulfone. Both enantiomers of the sulfoxide are obtained.

The sulfur-containing 4'- and 4"-groups can be oxidized to the corresponding sulfinyl and sulfonyl groups in a solvent such as a chlorinated hydrocarbon, THF, ether, or lower alcohol, preferably methylene chloride.

An oxidizing agent such as a peracid, preferably m-chloroperbenzoic acid, is added to a solution of the 4''- or 4'-substituted avermectin. By varying the temperature (from −30° C. to room temperature) and the number of equivalents of oxidizing agent, the relative yields of the sulfoxide and sulfone can be controlled. The products are separated and isolated using techniques known to those skilled in the art.

Further modifications of the side chain can be accomplished when a thio-alcohol is used as the nucleophile. The hydroxyl group of the alcohol on the sulfur-containing side chain can undergo any of the reactions and chemistry that is possible at the 4''- or 4'-hydroxy group, including, but not limited to, those described herein.

Following the desired substitution and modification at the 4''-position, the 5-hydroxy group is deprotected and, if desired, modifications of the molecule at the 5-position can occur.

The foregoing reactions carried out at the 4''-position of the avermectin can be carried out at the 4'-position of the avermectin monosacchoride to affect the correspondingly substituted monosacchoride derivatives.

The preparation of additional derivatives of the various reactive substituents can also be carried out using procedures well known to those skilled in the art. See for example U.S. Pat. No. 4,906,619 to Eskola et al, for the preparation of various alkylated avermectins; U.S. Pat. No. 4,427,663 to Mrozik for the preparation of various 4'- or 4''- keto or amino derivatives; U.S. Pat. No. 4,201,861 to Mrozik et al, for the preparation of various, acylated avermectins; U.S. Pat. Nos. Re. 32006 and Re. 32034 to Chabala et al for the preparation of various 13-substituted and 13-unsubstituted avermectins; U.S. Pat. No. 4,200,981 to Fisher et al for the preparation of various 5-alkylated compounds; and U.S. Pat. No. 4,895,837 to Mrozik for a discussion of various procedures for the protection of avermectin compounds.

The instant compounds are potent endo-and ecto-antiparasitic agents against parasites particularly helminths, ectoparasites, insects, and acarides, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camels, llamas, reindeer, laboratory animals, furbearing animals, zoo animals and exotic species and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs and cats, Nematospiroides, Syphacia, Aspiculuris in rodents, arthropod ectoparasites of animals and birds such as ticks, mites, lice, fleas, blowflies, in sheep Lucilia sp., biting insects and such migrating diperous larvae as Hypoderma sp. cattle, Gastrophilus in horses, and Cuterebra sp. in rodents and nuisance flies including blood feeding flies and filth flies.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly *Musca domestica* as well as fleas, house dust mites, termites and ants.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acerage infested with fire ant nests. The compounds are scattered above the infested area in low levels in bait formulations which are brought back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally including one or more additional active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area application, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or other arthropod pests.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting arthropods in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired antiparasitic result.

In using the compounds of this invention, the individual compounds may be prepared and used in that form. Alternatively, mixtures of the individual compounds may be used, or other active compounds not related to the compounds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

EXAMPLE 1

4'',5-Di-O-t-Butyldimethylsilyl-Avermectin B2a

To a solution of 58.2 g (65 mmol) of dried avermectin B2a in 400 mL of sieve-dried dimethylformamide and 30 mL of freshly distilled triethylamine was added a solution of 29.8 g (198 mmol, 3 equiv.) of t-butyldimethylsilyl chloride in 200 mL of dichloromethane. The mixture was stirred at room temperature 16 hours then poured into ice water and extracted with dichloromethane. The organic phases were combined and washed with water, brine, and dried over magnesium sulfate. Evaporation of the solvent afforded an oil which was purified by silica gel liquid chromatography using 20% ethyl acetate-hexanes to yield 34.2 g of 4'',5-di-O-t-butyldimethylsilylavermectin B2a characterized by its NMR and mass spectra.

EXAMPLE 2

4'',5-Di-O-t-Butyldimethylsilyl-23-oxo-Avermectin B2a

A 5-L 3-neck flask equipped with a thermometer, mechanical stirrer, and dropping funnel was charged with 400 mL of dichloromethane and 16 mL (0.185 mol) of oxalyl chloride. The solution was cooled to $-70°$ C., under nitrogen while a solution of 25 mL (0.350 mol) of dimethylsulfoxide in 200 mL of dichloromethane was added dropwise over 30 minutes keeping the internal temperature below $-65°$ C. The mixture was stirred at $-70°$ C. for 1 hour. A solution of 114.75 g (0.103 mmol) of 4'',5-di-O-t-butyldimethylsilyl-avermectin B2a in 900 mL of dichloromethane was then added dropwise over 45 minutes keeping the temperature of the mixture below $-65°$ C. After an additional 2 hours at $-70°$ C., 115 mL of triethylamine was added dropwise over 10 minutes again keeping the temperature below $-65°$ C. The reaction was then stirred at approximately 10° C. for 1 hour before the solvent was removed in vacuo. The residue was taken up in 1.5 L of ether and washed with 500 mL of water. The aqueous layer was extracted with 500 mL of ether. The combined ether layers were washed sequentially with $2\times1$ L of water, 1 L of saturated sodium bicarbonate, and 1 L of brine, then dried over magnesium sulfate. The solvent was removed to afford 100 g of yellow foam purified by column chromatography (4 kg silica gel, eluted with 5-25% ethyl acetatehexane eluant). The product was obtained as a yellow foam (101 g, 88% yield). NMR (300 MHz, TMS) $\delta 0.08$ (d, J=6 Hz), 0.14 (s), 0.9 (s), 0.93 (s), 0.98 (m), 1.16 (d, J=7 Hz), 1.2 (d, J=Hz), 1.24 (d, J=7 Hz), 1.45 (s), 1.5 (m), 1.8 (s), 2.22 (m), 2.44 (m), 3.12 (t, J=9 Hz), 3.2 (t, J=9 Hz), 3.32 (s), 3.42 (s), 3.6 (m), 3.81 (d, J=6 Hz), 3.93 (s), 3.98 (sh s), 4.44 (d, J=6 Hz), 4.62 (dq, J=2,14 Hz), 4.74 (d, J=3 Hz), 4.93 (t, J=7 Hz), 5.3 (m), 5.7 (m), 5.8 (m); mass spec: FAB 1123 (M+Li).

EXAMPLE 3

4'',5-Di-O-t-Butyldimethylsilyl-7-O-trimethylsilyl-23-O-trimethylsilyloxy-Avermectin B1a To a solution of 101 mg (0.09 mmol) of 4'',5-di-O-t-butyldimethylsilyl-23-oxo-avermectin B2a in 2 mL of distilled tetrahydrofuran at $-78°$ C. was added 0.400 mL of a 1.0M solution of lithium bis(trimethylsilyl)amide in a mixture of hexanes. The mixture was stirred at $-78°$ C., under argon, for 1 hour before 0.20 mL of the supernatant of a centrifuged 1:3 mixture of triethylamine and trimethylchlorosilane was added dropwise via a syringe. After another 30 minutes, 2 ml of a saturated aqueous sodium bicarbonate solution was added and the mixture was allowed to warm to room temperature. The reaction mixture was then partitioned between water and ether and the ethereal extracts were combined and dried over magnesium sulfate. Filtration and evaporation of the ther afforded 120 mg of 4'',5-di-O-t-butyldimethylsilyl-7-O-trimethylsilyl-23-O-trimethylsilyloxy-avermectin B1a characterized by its NMR $\delta 0.08$ (d, J=6 Hz), 0.12 (s), 0.18 (s), 0.88 (s), 0.92 (s), 1.18 (d, J=8 Hz), 1.23 (d, J=8 Hz), 1.26 (d, J=8 Hz), 1.5 (s), 1.51 (m), 1.78 (s), 2.3 (m), 2.58 (m), 3.12 (t, J=9 Hz), 3.22 (t, J=9 Hz), 3.25 (s), 3.32 (s), 3.4 (s), 3.8 (d, J=6 Hz), 3.82 (m), 3.98 (s), 4.39 (d, J=4 Hz), 4.6 (q, J=16 Hz), 4.68 (sh d, J=2 Hz, C22H), 4.8 (d, J=3 Hz), 4.9 (m), 5.1 (m), 5.25 (d, J=3 Hz), 5.45 (s), 5.7 (m).

EXAMPLE 4

4'',5-Di-O-t-Butyldimethylsilyl-7-O-trimethylsilyl-22-hydroxy-23-oxo-Avermectin B2a To a solution of 135 mg (0.107 mmol) of 4'',5-Di-O-t-butyldimethylsilyl-7-O-trimethylsilyl-23-O-trimethylsilyloxy-Avermectin B1a in 2 mL of dichloromethane was added a solution of 21 mg (0.12 mmol) of m-chloroperbenzoic acid in 1 mL of dichloromethane in one portion. After 20 minutes at 20° C., 0.2 mL of dimethylsulfide was added. The mixture was stirred another 30 minutes before the addition of aqueous sodium bicarbonate and extraction with ethyl acetate. The combined organic fractions were dried, filtered, and evaporated to afford 150 mg of solid. This product mixture was separated by preparative thin layer chromatography (20% ethyl actate-hexane) to afford 40 mg of 4'',5-Di-O-t-butyldimethylsilyl-7-O-trimethylsilyl-22-hydroxy-23-oxo-Avermectin B2a. NMR $\delta 0.08$ (d, J=6 Hz), 0.14 (s), 0.88 (s), 0.92 (s), 0.96 (d, J=6 Hz), 0.98 (d, J=6 Hz), 1.16 (d, J=7 Hz), 1.20 (d, J=6 Hz), 1.23 (d, J=6 Hz), 1.43 (s), 1.50 (s), 1.52 (m), 1.78 (s), 2.24 (m), 2.4 (dd, J=6,12 Hz), 2.58 (m), 3.12 (t, J=9 Hz), 3.22 (t, J=9 Hz), 3.3 (s), 3.32 (s), 3.4 (s), 3.62 (m), 3.82 (m), 3.82 (d, J=6 Hz), 3.92 (d, J=7 Hz), 3.97 (s), 4.38 (d, J=3 Hz), 4.6 (q, J=15 Hz), 4.77 (d, J=3 Hz), 4.83 (m), 5.05 (br d, J=7 Hz), 5.25 (d, J=3 Hz), 5.5 (s), 5.7 (m); mass spec. FAB 1212 (M+Li+H).

EXAMPLE 5

Preparation of aldehyde-acid

To a solution of 600 mg (0.5 mmol) of 4'',5-Di-O-t-butyldimethylsilyl-7-O-trimethysilyl-22-hydroxy-23-oxo-Avermectin B2a in 6 mL of benzene in an aluminum foil-covered glass vial was added 400 mg (0.9 mmol) of lead tetraacetate in one portion. After 30 minutes at 20° C., the solution was poured into a separatory funnel containing 12 mL of water and 600 mg of sodium sulfite. The mixture was then shaken and extracted with ethyl acetate. The combined extracts were dried (MgSO$_4$), filtered, and evaporated to afford 600 mg of solid. Flash chromatography through a column of silica gel eluting with 2:1 hexane:ethyl acetate, then acetone afforded 250 mg of starting material and 230 mg of aldehyde-acid. NMR $\delta 0.08$ (d, J=6 Hz), 0.13 (s), 0.89 (s), 0.92 (s), 1.15 (d, J=6 Hz), 1.18 (d, J=6 Hz), 1.20 (d, J=6 Hz), 1.26 (d, J=6 Hz), 1.5 (s), 1.53 (m), 1.78 (s), 2.3 (m), 2.78 (br s), 3.13 (t, J=9 Hz), 3.23 (t, J=9 Hz), 3.23 (s), 3.32 (s), 3.36 (m), 3.42 (br s), 3.68 (m), 3.81 (m), 3.82 (d, J=6 Hz), 3.98 (s), 4.38 (s), 4.6 (q, J=15 Hz), 4.79 (d, J=2 Hz), 4.86 (br s), 5.12 (br s), 5.3 (s), 5.44 (s), 5.7 (m).

EXAMPLE 6

Transketalization of Aldehyde-acid to Methoxy Aldehyde (III) and 2R,3R,4S-2,4-dimethyl-3-hydroxyhexanoic acid To a solution of 8 g of pyridinium tosylate in 80 mL of dry methanol was added 16.3 g of the aldehyde-acid from Example 5. The mixture was stirred at 20° C. for 1.5 hours before 4 mL of triethylamine was added. The mixture was then transferred to a separatory funnel containing 4.4 g of sodium bicarbonate and 500 mL of water. The mixture was extracted with ether and the aqeuous layer was then acidified with 2N HCl and extracted with ethyl acetate to recover 1.6 g of 2R,3R,4S-2,4-dimethyl-3-hydroxyhexanoic acid as an amber oil. The ether extracts were combined and dried over magnesium sulfate. Filtration and evaporation of the solvent afforded 15.5 g of solid as a 1:1:1 mixture of methoxy ketals and the aldehyde-acid in addition to some minor products with a slower Rf than the methoxy ketal but faster than the aldehyde-acid. The mixture was separated by flash column chromatography on 550 g of silica gel eluted with 3:1 and then 2:1 hexane: ethyl acetate to yield 5.1 g and 4.0 g and 3.9 g of the methoxy ketals each characterized by NMR and mass spectroscopy. NMR of methoxy-ketal A: $\delta$0.08 (d, J=6 Hz), 0.12 (s), 0.14 (s), 0.88 (s), 0.92 (s), 1.17 (d, J=7 Hz), 1.21 (d, J=7 Hz), 1.25 (d, J=7 Hz), 1.5 (m), 1.51 (s), 1.78 (s), 2.3 (m), 2.5 (m), 3.13 (t, J=9 Hz), 3.22 (t, J=9 Hz), 3.28 (sh d, J=2 Hz), 3.32 (s), 3.38 (s), 3.44 (s), 3.65 (m), 3.82 (d, J=6 Hz), 3.98 (s), 4.38 (d, J=3 Hz), 4.6 (dq, J=2,15 Hz), 4.7 (m), 4.78 (d, J=3 Hz), 5.12 (d, J=11 hz), 5.30 (d, J=3 Hz), 5.48 (s), 5.57 (m), 5.75 (dd, J=11,16 Hz), 9.37 (s). NMR of methoxy ketal B: $\delta$0.08 (d, J=6 hz), 0.13 (s), 0.88 (s), 0.90 (m), 0.92 (s), 1.18 (d, J=7 Hz), 1.21 (d, J=7 Ha), 1.26 (d, J=6 Hz), 1.42 (s), 1.5 (m), 1.52 (s), 1.6 (m), 1.78 (s), 1.90 (d, J=12 Hz), 2.35 (m), 2.58 (tt, J=6,2 Hz), 3.13 (t, J=9 Hz), 3.22 (t, J=9 Hz), 3.25 (s), 3.28 (s), 3.32 (s), 3.43 (s), 3.66 (m), 3.82 (d, J=6 Hz), 3.84 (m), 3.99 (s), 4.38 (d, J=3 Hz), 4.60 (dq, J=2,15 Hz), 4.80 (d, J=3 Hz), 4.90 (m), 5.15 (dd, J=5,12 Hz), 5.29 (d, J=3 Hz), 5.46 (s), 5.57 (m, J=9 Hz), 5.63 (d, J=12 Hz), 5.76 (dd, J=12,15 Hz), 9.39 (s). The stereochemical assignment at C21 for the methoxy ketal isomers A and B was based on the nonreversible conversion of A to B when each pure isomer was resubjected to acidic methanol. Isomer B being the thermodynamically stable isomer has been assigned the axial methoxy/equitorial formyl configuration. The chiral acid was esterified with excess diazomethane and purified by flash chromatography with 15% ethyl acetate-hexane to yield 1 g of methyl ester $[\alpha]_D = -9.5°$, c=8.9 g/dL dichloromethane, characterized by its NMR spectrum.

EXAMPLE 7

Preparation of 4'',5-bis-O-tert-butyldimethylsilyl-7-O-trimethylsilyl-21-methoxy-21,25-seco-24-desmethyl-25-des(2-butyl)-23,24,25-nor-22-trifluoromethanesulfonate-Avermectin B$_1$ (Va)

520 mg Methoxy-aldehyde IV (509 μmol) was dissolved in 10 mL methanol at 0° C. to which was added 85 mg NaBH$_4$ (2.5 mmol). After 10 min at 0° C., 0.5 mL acetone was added to the reaction and the solution was poured into 30 mL saturated NH$_4$Cl, extracted with methylene chloride and dried (MgSO$_4$). The solution was filtered and concentrated under reduced pressure. Pure alcohol (390 mg, 75%) was obtained by flash chromatography on silica gel using 6:4 hexanes:EtOAc as eluant. This alcohol was dissolved in 3 mL methylene chloride at 0° C. to which was added 35 μL diisopropylethyl amine (200 μmol), 25 mg 4-dimethylaminopyridine (200 μmol) and 25 mL (CF$_3$SO$_2$)$_2$O (150 μmol). After 15 min at 0° C., the reaction was filtered through a 1.5 inch plug of silica gel using 6:4 hexanes:EtOAc as eluant to yield 375 mg Va (85%). This material was a pale yellow solid following lyophilization from benzene (hydroscopic!).

EXAMPLE 8

Preparation of 4'',5-bis-O-tert-butyldimethylsilyl-7-O-trimethylsilyl-21-(methyl 2R,3R,4S-2,4-dimethylhexanoate)-21,25-seco-24-desmethyl-25-des(2-butyl)-22-trifluoromethanesulfonate-Avermectin B$_1$ (Vb)

2.0 g Aldehyde-ester III (1.62 mmol) was dissolved in 20 mL methanol at 0° C. to which was added 65 mg NaBH$_4$ (1.71 mmol). After 15 min, the solution was poured into 40 mL saturated NH$_4$Cl, extracted with EtOAc, washed with brine and dried (MgSO$_4$). The solution was filtered and concentrated under reduced pressure. The resultant alcohol was purified by flash chromatography on silica gel to yield 1.56 g alcohol (78%). 832 mg of this alcohol (674 mmol) was dissolved in 5 mL methylene chloride at $-30°$ C. to which was added 247 mg 4-dimethylaminopyridine (2.02 mmol), 261 mg diisopropylethyl amine (2.02 mmol) and 285 mg (CF$_3$SO$_2$)$_2$O (1.01 mmol). The solution was warmed to 0° C. and stirred for 10 min. The solution was filtered directly through a 1.5 inch plug of silica gel using 1:3 EtOAc:hexanes as eluant. Pure Vb (801 mg, 87%) was obtained as a pale yellow solid after lyophilization from benzene (hydroscopic!).

EXAMPLE 9

Preparation of 4'',5-bis-O-tert-butyldimethylsilyl-7-O-trimethylsilyl-21-methoxy-21,25-seco-24-desmethyl-25-des(2-butyl)-23-nor-25-hydroxy-23-this-invermectin B1 (VIa)

190 mg Triflate Va (164 μmol) was dissolved in 3 mL dimethylformamide at RT. To this was added 200 μL 2-mercaptoethanol, 100 mg K$_2$CO$_3$, and 10 mg 18-crown-6. The solution was stirred at RT for 1 hr, poured into 40 mL 1:1 water:saturated NaHCO$_3$, extracted with methylene chloride and dried (MgSO$_4$). The solution was filtered and concentrated under reduced pressure. Pure VIa (145 mg, 82%) was obtained by flash chromatography on silica gel using 1:1 hexanes:EtOAc as eluant.

EXAMPLE 10

Preparation of 4'',5-bis-O-tert-butyldimethylsilyl-7-O-trimethylsilyl-21-(methyl 2R,3R,4S-2,4-dimethylhexanoate)-21,25-seco-24-desmethyl-25-des(2-butyl)-23-nor-23-thia-25-hydroxy-ivermectin B1 (VIb)

800 mg Triflate Vb (585 μmol) was dissolved at RT in 5 mL dimethylformamide to which was added 20 mg 18-crown-6, 718 mg mercaptoethanol and 800 mg K$_2$CO$_3$. After 30 min at RT, the solution was poured into 20 mL saturated NaHCO$_3$, extracted with EtOAc and dried (MgSO$_4$). The solution was filtered and concentrated to approximately 5 mL then filtered through a 1.5 inch plug of silica gel using 1:1 hexanes:EtOAc as eluant. The solvents were removed under reduced pressure and pure VIb (646 mg, 85%) was obtained after flash chromatography on silica gel using 1:3 to 2:3 EtOAc:hexanes gradient elution.

EXAMPLE 11

Preparation of 4",5-bis-O-tert-butyldimethylsilyl-7-O-trimethylsily-21-methoxy-21,25-seco-24-desmethyl-25-des(2-butyl)-23-nor-25-phenyl-25-hydroxy-23-thia-ivermectin B1 (VIc)

105 mg Aldehyde XI (91 μmol) was placed in 3 mL THF at 0° C. to which was added 61 μL PhMgBr (3M in THF, 182 μmol). After 30 min at 0° C., the solution was poured into 10 mL saturated NH₄Cl, extracted with EtOAc and dried (MgSO₄). Pure VIc (61 mg, 54%) was obtained by flash chromatography on silica gel with 2:1 hexanes:EtOAc as eluant.

EXAMPLE 12

Preparation of 4",5-bis-O-tert-butyldimethylsilyl-7-O-trimethylsilyl-21-methoxy-21,25-seco-24-desmethyl-25-des(2-butyl)-23-nor-25-iso-propyl-25-hydroxy-23-thia-ivermectin B1 (VId)

200 mg Aldehyde XI (173 μmol) was placed in 4 mL THF at 0° C. to which was added 260 μL i-PrMgBr (2M in THF, 519 μmol). After 30 min at 0° C., the solution was poured into 15 mL saturated NH₄Cl, extracted with EtOAc and dried (MgSO₄). Pure VId (195 mg, 93%) was obtained by flash chromatography on silica gel with 2:1 hexanes:EtOAc as eluant.

EXAMPLE 13

Preparation of 4",5-bis-O-tert-butyldimethylsilyl-7-O-trimethylsilyl-21-methoxy-21,25-seco-24-desmethyl-25-des(2-butyl)-23-nor-25-cyclohexyl-25-hydroxy-23-thia-ivermectin B1 (VIe)

200 mg Aldehyde XI (173 μmol) was placed in 4 mL THF at 0° C. to which was added 260 μL c-C₆H₁₁MgBr (2M in THF, 519 μmol). After 30 min at 0° C., the solution was poured into 15 mL saturated NH₄Cl, extracted with EtOAc and dried (MgSO₄). Pure VIe (165 mg, 77%) was obtained by flash chromatography on silica gel with 2:1 hexanes:EtOAc as eluant.

EXAMPLE 14

Preparation of 4",5-bis-O-tert-butyldimethylsilyl-7-O-trimethylsilyl-21-(methyl 2R,3R,4S-2,4-dimethylhexanoate)-21,25-seco-24-desmethyl-25-des(2-butyl)-23-nor-25-tert-butyl-25-hydroxy-23-thia-ivermectin B1 (VIf)

127 mg Ketone XIIIc (94 μmol) was dissolved in 5 mL methanol at 0° C. to which was added 40 mg NaBH₄. After 30 min at 0° C., the reaction was quenched with acetone, diluted with 2 mL saturated NH₄Cl, extracted with EtOAc and dried (MgSO₄). The solution was filtered and concentrated under reduced pressure. Pure VIf (120 mg, 94%) was obtained after flash chromatography on silica gel using 2:2:7 tert-BuOMe:CH₂Cl₂:hexanes.

EXAMPLE 15

Preparation of 4",5-bis-O-tert-butyldimethylsilyl-7-O-trimethylsilyl-24-desmethyl-25-des(2-butyl)-23-nor-23-thia-ivermectin B1 (VIIa)

120 mg Alcohol VIa (111 μmol) was placed in 5 mL methylene chloride at RT to which was added 5 mg p-toluenesulfonic acid. After 15 min, the reaction was poured into 10 mL saturated NaHCO₃, extracted with methylene chloride and dried (MgSO₄). The solution was filtered and concentrated under reduced pressure. Pure VIIa (101 mg, 86%) was obtained as a colorless glass by flash chromatography on silica gel using 2:1 hexanes:EtOAc as eluant.

EXAMPLE 16

Preparation of 4",5-bis-O-tert-butyldimethylsilyl-7-O-trimethylsilyl-24-desmethyl-25-des(2-butyl)-23-nor-25-phenyl-23-thia-ivermectin B1 (VIIb)

70 mg Alcohol VIc (60 μmol) was placed in 2.5 mL methylene chloride at RT to which was added 8 mg pyridinium p-toluenesulfonic acid and 2 mg p-toluenesulfonic acid. After 30 min at RT, 200 μL triethyl amine was added, the solution concentrated under reduced pressure and purified with no further workup by flash chromatography on silica gel using 3:1 hexanes:EtOAc as eluant. Sulfide VIIb (52 mg, 76%) was obtained as a white powder.

EXAMPLE 17

Preparation of 4",5-bis-O-tert-butyldimethylsilyl-7-O-trimethylsilyl-24-desmethyl-25-des(2-butyl)-23-nor-25-R-phenyl-23-thia-ivermectin B1 (VIIc)

54 mg Ketone XIIIb (44 μmol) was dissolved in toluene at −30° C. to which was added 5 mg (R)-(+)-oxazaborolidine.BH₃ (1.7 μmol) followed by 200 μL BH₃.SMe₂ (0.5M in THF). After 1 hr, the solution was brought to 0° C. After 40 min at 0° C., the reaction was quenched with 10 mL saturated NH₄Cl, extracted with EtOAc and dried (MgSO₄). The solution was filtered and concentrated under reduced pressure. With no further purification, the resultant alcohol was dissolved in 2 mL methylene chloride to which was added 50 mg pyridinium p-toluenesulfonic acid and 5 mg p-toluenesulfonic acid. The reaction was quenched with 2 mL saturated NaHCO₃, extracted with EtOAc and dried (MgSO₄). Pure VIIc (47 mg, 89%) was obtained as a white powder after flash chromatography on silica gel using 3:1 hexanes:EtOAc as eluant.

EXAMPLE 18

Preparation of 4",5-bis-O-tert-butyldimethylsilyl-7-O-trimethylsilyl-24-desmethyl-25-des(2-butyl)-23-nor-25-iso-propyl-23-thia-ivermectin B1 (VIId)

195 mg Alcohol VId (162 μmol) was placed in 4 mL methylene chloride at Rt to which was added 10 mg pyridinium p-toluenesulfonic acid and 5 mg p-toluenesulfonic acid. After 15 min at RT, 300 μL triethyl amine was added and the solution purified with no further workup by flash chromatography on silica gel using 2:1 hexanes:EtOAc as eluant. Pure VIId (130 mg, 68%) was thus obtained as a white powder.

EXAMPLE 19

Preparation of
4″,5-bis-O-tert-butyldimethylsilyl-7-O-trimethylsilyl-24-desmethyl-25-des(2-butyl)-23-nor-25-cyclohexyl-23-thia-ivermectin B1 (VIIe)

165 mg Alcohol VIe (133 μmol) was placed in 4 mL methylene chloride at RT to which was added 10 mg pyridinium p-toluenesulfonic acid and 5 mg p-toluenesulfonic acid. After 15 min at RT, 300 μL triethyl amine was added and the solution purified with no further workup by flash chromatography on silica gel using 2:1 hexanes:EtOAc as eluant. Pure VIIe (130 mg, 81%) was thus obtained as a white powder.

EXAMPLE 20

Preparation of
4″,5-bis-O-tert-butyldimethylsilyl-7-O-trimethylsilyl-24-desmethyl-25-des(2-butyl)-23-nor-25-tert-butyl-23-thia-ivermectin B1 (VIIf)

120 mg Alcohol VIf (94 μmol) was placed in 2 mL methylene chloride at Rt to which was added 108 mg pyridinium p-toluenesulfonic acid and 7 mg p-toluenesulfonic acid. After 10 min at RT, 200 μL triethyl amine was added and the solution purified with no further workup by flash chromatography on silica gel using 3:1 hexanes:EtOAc as eluant. Pure VIIf (108 mg, 97%) was thus obtained as a white powder.

EXAMPLE 21

Preparation of
24-desmethyl-25-des(2-butyl)-23-nor-23-thia-ivermectin B1

101 mg Tris-silyl ether VIIa (96 μmol) was placed in 5 mL THF at RT to which was added 1 mL HF.pyridine solution (25 g HF.pyridine, 10 mL pyridine, 25 mL THF). After 48 hrs, the solution was poured into 40 mL 1:1 water:Et$_2$O. The layers were separated and neutralized separately with saturated NaHCO$_3$. The aqueous layers were pooled and extracted with Et$_2$O. The organic layers were combined and dried (MgSO$_4$). The solution was filtered and concentrated under reduced pressure. Pure deprotected 24-desmethyl-25-des(2-butyl)-23-nor-22-hydro-23-thia-ivermectin B1 (55 mg, 70%) was obtained by flash chromatography on silica gel using 3:1 EtOAc:hexanes as eluant.

EXAMPLE 22

Preparation of
24-desmethyl-25-des(2-butyl)-23-nor-25-iso-propyl-23-thia-ivermectin B1

60 mg Tris-silyl ether VIIc (53 μmol) was placed in 4 mL THF at RT to which was added 1 mL HF.pyridine solution (25 g HF.pyridine, 10 mL pyridine, 25 mL THF). After 48 hrs, the solution was poured into 40 mL 1:1 water:Et$_2$O. The layers were separated and neutralized separately with saturated NaHCO$_3$. The aqueous layers were pooled and extracted with Et$_2$O. The organic layers were combined and dried (MgSO$_4$). The solution was filtered and concentrated under reduced pressure. Pure deprotected 24-desmethyl-25-des(2-butyl)-23-nor-25-phenyl-23-thia-ivermectin B1 (55 mg, 70%) was obtained by flash chromatography on silica gel using 3:1 EtOAc:hexanes as eluant.

EXAMPLE 23

Preparation of
24-desmethyl-25-des(2-butyl)-23-nor-25-iso-propyl-23-thia-ivermectin B1

130 mg Tris-silyl ether VIId (111 μmol) was placed in 4 mL THF at RT to which was added 1 mL HF.pyridine solution (25 g HF.pyridine, 10 mL pyridine, 25 mL THF). After 48 hrs, the solution was poured into 40 mL 1:1 water:Et$_2$O. The layers were separated and neutralized separately with saturated NaHCO$_3$. The aqueous layers were pooled and extracted with Et$_2$O. The organic layers were combined and dried (MgSO$_4$). The solution was filtered and concentrated under reduced pressure. Pure deprotected 24-desmethyl-25-des(2-butyl)-23-nor-22-hydro-25-iso-propyl-23-thia-ivermectin B1 (91 mg, 94%) was obtained by flash chromatography on silica gel using 3:1 EtOAc:hexanes as eluant.

EXAMPLE 24

Preparation of
24-desmethyl-25-des(2-butyl)-23-nor-25-cyclohexyl-23-thia-ivermectin B1

144 mg Tris-silyl ether VIIe (119 μmol) was placed in 4 mL THF at RT to which was added 1 mL HF.pyridine solution (25 g HF.pyridine, 10 mL pyridine, 25 mL THF). After 48 hrs, the solution was poured into 40 mL 1:1 water:Et$_2$O. The layers were separated and neutralized separately with saturated NaHCO$_3$. The aqueous layers were pooled and extracted with Et$_2$O. The organic layers were combined and dried (MgSO$_4$). The solution was filtered and concentrated under reduced pressure. Pure deprotected 24-desmethyl-25-des(2-butyl)-23-nor-25-cyclohexyl-23-thia-ivermectin B1 (91 mg, 84%) was obtained by flash chromatography on silica gel using 3:1 EtOAc:hexanes as eluant.

EXAMPLE 25

Preparation of
24-desmethyl-25-des(2-butyl)-23-nor-25-tert-butyl-23-thia-ivermectin B1

108 mg Tris-silyl ether VIIf (91 μmol) was placed in 4 mL THF at RT to which was added 1 mL HF.pyridine solution (25 g HF.pyridine, 10 mL pyridine, 25 mL THF). After 48 hrs, the solution was poured into 40 mL 1:1 water:Et$_2$O. The layers were separated and neutralized separately with saturated NaHCO$_3$. The aqueous layers were pooled and extracted with Et$_2$O. The organic layers were combined and dried (MgSO$_4$). The solution was filtered and concentrated under reduced pressure. Pure deprotected 24-desmethyl-25-des(2-butyl)-23-nor-25-tert-butyl-23-thia-ivermectin B1 (73 mg, 90%) was obtained by flash chromatography on silica gel using 6:4 EtOAc:hexanes as eluant.

EXAMPLE 26

Preparation of
24-desmethyl-25-des(2-butyl)-23-nor-23-sulfinyl-ivermectin B1 (VIIIa) and
24-desmethyl-25-des(2-butyl)-23-nor-23-sulfonyliver-mectin B1 (IXa)

40 mg of 24-desmethyl-25-des(2-butyl)-23-nor-22-hydro-23-thia-ivermectin B1 (48 μmol) was cooled to 0° C. in 2 mL methylene chloride to which was added 15 mg meta-chloroperbenzoic acid (72 μmol). After 10 min at 0° C., the solution was warmed to RT and stirred for 1 hr. The solution was purified without workup by flash chromatography on silica gel using EtOAc to elute IXa (6 mg, 14%) and 1:9 MeOH:EtOAc to elute VIIIa (34 mg, 84%). Both VIIIa and IXa were white powders.

EXAMPLE 27

Preparation of 24-desmethyl-25-des(2-butyl)-23-nor-25-phenyl-23-sulfinyl-ivermectin B1 (VIIIb) and 24-desmethyl-25-des(2-butyl)-23-nor-22-hydro-25-phenyl-23-sulfonyl-ivermectin B1 (IXb)

36 mg of 24-desmethyl-25-des(2-butyl)-23-nor-25-iso-propyl-23-thia-ivermectin B1 (40 μmol) was cooled to 0° C. in 2 mL methylene chloride to which was added 15 mg meta-chloroperbenzoic acid (72 μmol). After 10 min at 0° C., the solution was warmed to RT and stirred for 1 hr. The solution was purified without workup by flash chromatography on silica gel using EtOAc to elute IXb (12 mg, 34%) and 1:9 MeOH:EtOAc to elute VIIIb (21 mg, 59%). Both VIIIb and IXb were white powders.

EXAMPLE 28

Preparation of 24-desmethyl-25-des(2-butyl)-23-nor-25-iso-propyl-23-sulfinyl-ivermectin B1 (VIIIc) and 24-desmethyl-25-des(2-butyl)-23-nor-25-iso-propyl-23-sulfonyl-ivermectin B1 (IXc)

27 mg of 24-desmethyl-25-des(2-butyl)-23-nor-25-iso-propyl-23-thia-ivermectin B1 (31 μmol) was cooled to 0° C. in 2 mL methylene chloride to which was added 15 mg meta-chloroperbenzoic acid (72 μmol). After 10 min at 0° C., the solution was warmed to RT and stirred for 1 hr. The solution was purified without workup by flash chromatography on silica gel using EtOAc to elute IXc (10 mg, 35%) and 1:9 MeOH:EtOAc to elute VIIIc (12 mg, 45%). Both VIIIc and IXc were white powders.

EXAMPLE 29

Preparation of 24-desmethyl-25-des(2-butyl)-23-nor-22-hydro-25-cyclohexyl-23-sulfinyl-ivermectin B1 (VIIId) and 24-desmethyl-25-des(2-butyl)-23-nor-25-cyclohexyl-23-sulfonyl-ivermectin B1 (IXd)

31 mg 24-desmethyl-25-des(2-butyl)-23-nor-25-cyclohexyl-23-thia-ivermectin B1 (34 μmol) was cooled to 0° C. in 2 mL methylene chloride to which was added 15 mg meta-chloroperbenzoic acid (72 μmol). After 10 min at 0° C., the solution was warmed to RT and stirred for 1 hr. The solution was purified without workup by flash chromatography on silica gel using EtOAc to elute IXd (17 mg, 53%) and 1:9 MeOH:EtOAc to elute VIIId (14 mg, 44%). Both VIIId and IXd were white powders.

EXAMPLE 30

Preparation of 4″,5-bis-O-tert-butyldimethylsilyl-7-O-trimethylsilyl-21-(methyl 2R,3R,4S-2,4-dimethylhexanoate)-21,25-seco-24-desmethyl-25-des(2-butyl)-23-nor-25-phenyl-23-thia-25-oxo-ivermectin B1 (XIIId)

210 mg Triflate Vb (154 μmol) was dissolved in 1 mL dimethylformamide at RT to which was added 5 mg 18-crown-6, 250 mg α-mercaptoacetophenone and 200 mg K$_2$CO$_3$. After 30 min, 2 mL saturated NaHCO$_3$ and 2 mL brine were added, the solution extracted with EtOAc and dried (MgSO$_4$). The solution was filtered and concentrated under reduced pressure. Pure XIIId (159 mg, 69%) was obtained as a white solid after flash chromatography on silica gel using 15:85 to 20:80 EtOAc:hexanes gradient elution.

EXAMPLE 31

Preparation of 4″,5-bis-O-tert-butyldimethylsilyl-7-O-trimethylsilyl-21-(methyl 2R,3R,4S-2,4-dimethylhexanoate)-21,25-seco-24-desmethyl-25-des(2-butyl)-23-nor-25-tert-butyl-23-thia-25-oxo-ivermectin B1 (XIIIe)

136 mg Triflate Vb (100 μmol) was dissolved in 2 mL dimethylformamide at RT to which was added 5 mg 18-crown-6, 249 mg α-mercaptopinacolone and 130 mg K$_2$CO$_3$. After 30 min, 2 mL saturated NaHCO$_3$ and 2 mL brine were added, the solution extracted with EtOAc and dried (MgSO$_4$). The solution was filtered and concentrated under reduced pressure. Pure XIIIe (127 mg, 94%) was obtained as a white solid after flash chromatography on silica gel using 4:1:1 to 3:1:1 hexanes:CH$_2$Cl$_2$:tert-BuOMe gradient elution.

EXAMPLE 32

Preparation of 4″,5-bis-O-tert-butyldimethylsilyl-7-O-trimethylsilyl-21-methoxy-21,25-seco-24-desmethyl-25-des(2-butyl)-23-nor-22-hydro-25-oxo-23-thia-ivermectin B1 (XI)

160 mg Alcohol VIa (138 μmol) was dissolved in 4 mL methylene chloride at RT to which was added 63 mg Dess-Martin reagent (150 μmol). After 20 min, the solution was purified without workup by flash chromatography on silica gel with 1:1 hexanes:EtOAc as eluant. Pure XI (105 mg, 66%) was thus obtained as a white powder.

EXAMPLE 33

Preparation of 4″,5-bis-O-tert-butyldimethylsilyl-7-O-trimethylsilyl-21-methoxy-21,25-seco-24-desmethyl-25-des(2-butyl)-23-nor-22-hydro-25-phenyl-25-oxo-23-thia-ivermectin B1 (XIIIb)

100 mg Alcohol VIc (81 μmol) was dissolved in 2 mL methylene chloride to which was added 75 mg Dess-Martin reagent (178 μmol). After 15 min, the solution was placed directly on a flash chromatography column without workup and eluted with 1:3 EtOAc:hexanes to yield 54 mg XIIIb (54%) as a white powder.

EXAMPLE 34

Preparation of 4″,5-bis-O-tert-butyldimethylsilyl-7-O-trimethylsilyl-21-(methyl 2R,3R,4S-2,4-dimethylhexanoate)-21,25-seco-24-desmethyl-25-des(2-butyl)-22-mercapto-ivermectin B1 (XII)

199 mg Triflate Vb (146 μmol) was dissolved in 2 mL dimethylformamide at RT to which was added 57 mg potassium thioacetate (500 μmol). After 1 hr, the solution was placed directly on a 1.5 inch silica gel plug and eluted with 1:3 EtOAc:hexanes to yield pure thioacetate (162 mg, 86%) as a white powder. The thioacetate (162 mg, 126 μmol) was dissolved in methanol at 0° C. to which was added 200 mg NaBH$_4$. The solution was poured into 20 mL saturated NH$_4$Cl, extracted with EtOAc and dried (MgSO$_4$). The solution was filtered and concentrated under reduced pressure. Pure XII (122 mg, 70%) was obtained as a white solid following flash chromatography on silica gel using 2:8 EtOAc:-hexanes as eluant.

EXAMPLE 35

Preparation of 23-nor-23-sulfonyl-24-desmethyl-25-des(2-butyl)-25-phenyl ivermectin B1 aglycone Add 200 mg 23-nor-23-sulfonyl-24-desmethyl-25-des(2-butyl)-25-phenyl ivermectin B1 to a 1% solution of sulfuric acid in 6 mL methanol at RT and stir the solution of 12 hrs. Pour the solution into saturated ice-cold NaHCO$_3$, extract with EtOAc and dry (MgSO$_4$). Filter and concentrate the solution under reduced pressure. Pure 23-nor-23-sulfonyl-24-desmethyl-25-des(2-butyl)-25-phenyl ivermectin B1 aglycone may be obtained following flash chromatography on silica gel.

EXAMPLE 36

Preparation of 23-nor-23-thia-24-desmethyl-25-des(2-butyl)-5-deoxy-5-ketoxime-25-sec-butyl ivermectin B1

Dissolve 200 mg 23-nor-23-thia-24-desmethyl-25-des(2-butyl)-25-sec-butyl ivermectin B1 in 4 mL EtOAc at RT and add to it 300 mg MnO$_2$. Stir the solution for 1 hr, then filter the solution through a bed of celite and concentrate the solution under reduced pressure. Pure 23-nor-23-thia-24-desmethyl-5-keto-25-des(2-butyl)-25-sec-butyl ivermectin B$_1$ may be obtained following flash chromatography on silica gel. Place 100 mg 23-nor-23-thia-24-desmethyl-5-keto-25-des(2-butyl)-25-sec-butyl ivermectin B$_1$ in 4 mL EtOAc and add 0.150 mL 1.0M zinc chloride in ether followed by 0.10 mL TMSONH$_2$. Stir for two hrs at RT, add 1 mL saturated NaHCO$_3$ and stir for 15 additional minutes. Dilute the solution with 4 mL water, extract with ethyl acetate and dry (MgSO$_4$). Filter and concentrate the solution under reduced pressure. Pure 23-nor-23-thia-24-desmethyl-25-des(2-butyl)-5-deoxy-5-ketoxime-25-sec-butyl ivermectin B1 may be obtained following flash chromatography on silica gel.

EXAMPLE 37

Preparation of 23-nor-23-sulfonyl-24-desmethyl-25-des(2-butyl)-5-O-tert-butyldimethylsilyl-25-tert-butyl ivermectin B1

Place 200 mg 23-nor-23-sulfonyl-24-desmethyl-25-des(2-butyl)-25-tert-butyl ivermectin B1 in 3 mL dimethylformamide at RT and add to it 66 mg imidazole and 73 mg tert-butyldimethylsilyl chloride. Stir for 2 hrs at RT and then pour into water, extract with EtOAc and dry (MgSO$_4$). Filter the solution and concentrate under reduced pressure. Pure 23-nor-23-sulfonyl-24-desmethyl-25-des(2-butyl)-5-O-tert-butyldimethylsilyl-25-tert-butyl ivermectin B1 may be obtained following flash chromatography on silica gel.

EXAMPLE 38

Preparation of 23-nor-23-sulfonyl-24-desmethyl-25des(2-butyl)-5-O-tert-butyldimethylsilyl-4″-oxo-25-tert-butyl ivermectin B1

Place 200 mg 23-nor-23-sulfonyl-24-desmethyl-25-des(2-butyl)-5-O-tert-butyldimethylsilyl-25-tert-butyl ivermectin B1 in 3 mL isopropyl acetate at −30° C. and to this solution add, sequentially, 0.056 mL diisopropylethylamine, 0.022 mL methyl sulfoxide and 0.044 mL phenylphosphonic dichloride. Warm this solution slowly to RT over 1 hr. Quench the reaction with 1 mL saturated NaHCO$_3$, extract with methylene chloride and dry (MgSO$_4$). Filter and concentrate the solution under reduced pressure. Pure 23-nor-23-sulfonyl-24-desmethyl-25-des(2-butyl)-5-O-tert-butyldimethylsilyl-4″-oxo-25-tert-butyl ivermectin B1 may be obtained following flash chromatography on silica gel.

EXAMPLE 39

Preparation of 23-nor-23-sulfonyl-24-desmethyl-25-des(2-butyl)-5-O-tert-butyldimethylsilyl-4″-deoxy-4″-amino-25-tert-butyl ivermectin B1

Place 100 mg 23-nor-23-sulfonyl-24-desmethyl-25-des(2-butyl)-5-O-tert-butyldimethylsilyl-4″-oxo-25-tert-butyl ivermectin B1 in 3 mL methanol with 160 mg ammonium acetate and to this add 12 mg sodium cyanoborohydride. Stir the reaction at RT for 1 hr and then pour into saturated NaHCO$_3$. Extract the organic products with EtOAc, dry (MgSO$_4$), filter and concentrate the solution under reduced pressure. Pure 23-nor-23-sulfonyl-24-desmethyl-25-des(2-butyl)-5-O-tert-bytyldimethylsilyl-4″-amino-25-tert-butyl ivermectin B1 may be obtained following flash chromatography on silica gel.

EXAMPLE 40

Preparation of 23-nor-23-sulfonyl-24-desmethyl-25-des(2-butyl)-5-O-tert-butyldimethylsilyl-4″-deoxy-4″-acetylamino-25-tert-butyl ivermectin B1

Place 50 mg 23-nor-23-sulfonyl-24-desmethyl-25-des(2-butyl)-5-O-tert-butyldimethylsilyl-4″-amino-25-tert-butyl ivermectin B1 in 2 mL methylene chloride at 0° C. and add 0.20 mL pyridine, 25 mg 4-dimethylaminopyridine and 0.10 mL acetic anhydride. After 3 hrs at 0° C., pure 23-nor-23-sulfonyl-24-desmethyl-25-des(2-butyl)-5-O-tert-butyldimethylsilyl-4″-acetylamino-25-tert-butyl ivermectin B1 may be obtained following flash chromatography on silica gel.

EXAMPLE 41

Preparation of 23-nor-23-sulfonyl-24-desmethyl-25-des(2-butyl)-4″-deoxy-4″-acetylamino-25-tert-butyl ivermectin B1

Place 25 mg 23-nor-23-sulfonyl-24-desmethyl-25-des(2-butyl)-5-O-tert-butyldimethylsilyl-4″-acetylamino-25-tert-butyl ivermectin B1 in 4 mL THF at RT and add 1 mL HF.pyridine solution (25 g HF.pyridine, 10 mL pyridine, 25 mL THF) and stir for 12 hrs. Pour the solution into 20 mL 1:1 water:Et$_2$O. Neutralize each layer with saturated NaHCO$_3$ and extract the aqueous layer with ether. Dry (MgSO$_4$) the combined organic layers. Filter the solution and concentrate it under reduced pressure. Pure 23-nor-23-sulfonyl-24-desmethyl-25-des(2-butyl)-4″-acetylamino-25-tert-butyl ivermectin B1 may be obtained following flash chromatography on silica gel.

What is claimed is:

1. The compound having the formula:

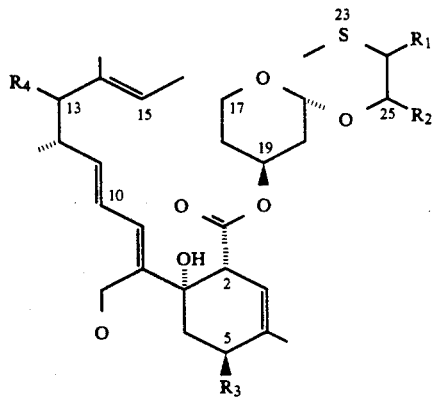

where

R$_1$ and R$_2$ are independently hydrogen, C$_1$-C$_{10}$ alkyl, C$_2$-C$_{10}$ alkenyl, C$_2$-C$_{10}$ alkynyl, C$_1$-C$_{10}$ alkoxy C$_1$-C$_{10}$ alkyl or C$_1$-C$_{10}$ alkylthio C$_1$-C$_{10}$ alkyl group; a C$_3$-C$_8$ cycloalkyl or C$_5$-C$_8$ cycloalkenyl group, either of which may optionally be substituted by methylene or from 1 to 3 of C$_1$-C$_4$ alkyl groups or halo atoms; phenyl, phenoxy, C$_1$-C$_{10}$ alkyl phenyl, C$_2$-C$_{10}$ alkenyl phenyl, C$_2$-C$_{10}$ alkynyl phenyl, substituted C$_1$-C$_{10}$ alkyl wherein the substituents independently are 1 to 3 of C$_1$-C$_5$ alkyl, C$_3$-C$_8$ cycloalkyl or substituted C$_1$-C$_{10}$ alkyl wherein the substituents are independently 1 to 3 of hydroxy, halogen, cyano, C$_1$-C$_5$ alkyl thio, C$_1$-C$_5$ alkyl sulfinyl, C$_1$-C$_5$ alkyl sulfonyl, amino, C$_1$-C$_5$ mono or dialkyl amino, C$_1$-C$_5$ alkanoyl amino or C$_1$-C$_5$ alkanoylthio; or a 3 to 6 membered oxygen or sulfur containing heterocyclic ring which may be saturated or fully or partly unsaturated and which may optionally be substituted independently by 1 to 3 of C$_1$-C$_5$ alkyl or halogen; or R$_3$ is hydroxy, C$_1$-C$_5$-alkoxy, hydroximino or —O—C$_1$-C$_5$ alkyl-hydroximino;

R$_4$ is hydrogen, halogen, hydroxy, C$_1$-C$_5$ alkanoyloxy, (C$_1$-C$_5$-alkoxy)$_n$ where n is 1-4,

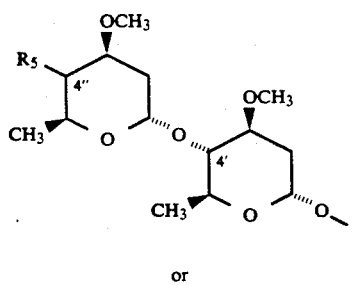

or

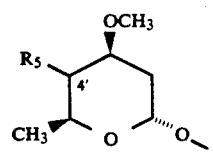

where R$_5$ is hydroxy, oxo, (C$_1$-C$_5$ alkyl)$_m$ amino, C$_1$-C$_5$ alkanoyl amino, (C$_1$-C$_5$ alkyl)(C$_1$-C$_5$ alkanoyl) amino, C$_1$-C$_5$ alkyl-S(O)$_m$, hydroxy substituted C$_1$-C$_5$ alkyl S(O)$_m$, where m is 0, 1 or 2 or (C$_1$-C$_5$-alkoxy)$_n$ where n=1-4.

2. A compound of claim 1 where:

R$_1$ and R$_2$ are independently hydrogen, C$_1$-C$_5$ alkyl, C$_2$-C$_5$ alkenyl, C$_1$-C$_5$ alkoxy, a C$_5$-C$_6$ cycloalkyl or C$_5$-C$_6$ cycloalkenyl group, either of which may optionally be substituted by methylene or from 1 to 3 of C$_1$-C$_4$ alkyl groups; phenyl, phenoxy, C$_1$-CH$_5$ alkyl phenyl, C$_2$-C$_5$ alkenyl phenyl, substituted C$_1$-C$_5$ alkyl wherein the substitutents independently are 1 to 3 of C$_1$-C$_3$ alkyl, C$_1$-C$_3$ alkyl thio, C$_1$-C$_3$ alkyl sulfinyl, C$_1$-C$_3$ alkyl sulfonyl, or a 5 to 6 membered oxygen or sulfur containing heterocyclic ring which may be saturated or fully or partly unsaturated; or R$_3$ is hydroxy, C$_1$-C$_3$-alkoxy, C$_1$-C$_3$-alkanoyloxy hydroximino or —O—C$_1$-C$_5$ alkyl-hydroximino;

R$_4$ is hydrogen, halogen, hydroxy, C$_1$-C$_3$-alkanoyloxy, (C$_1$-C$_3$ alkoxy), where n is 1-2,

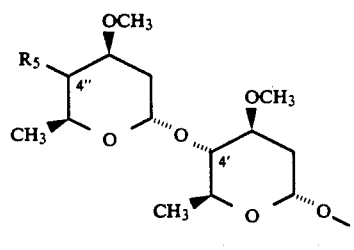

or

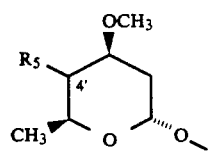

where R$_5$ is hydroxy, C$_1$-C$_3$ alkyl amino, C$_1$-C$_3$ alkanoyl amino, (C$_1$-C$_3$ alkyl)(C$_1$-C$_3$ alkanoyl) amino, C$_1$-C$_3$ alkyl-S(O)$_m$, hydroxy substituted C$_1$-C$_3$ alkyl S(O)$_m$, where m is 0, 1 or 2 or (C$_1$-C$_3$-alkoxy)$_n$ where n=1-4.

3. A compound of claim 2 where:

R$_1$ is hydrogen, C$_1$-C$_4$-alkyl;

R$_2$ is hydrogen, C$_1$-C$_5$ alkyl, C$_2$-C$_5$ alkenyl, C$_1$-C$_5$ alkoxy, a C$_5$-C$_6$ cycloalkyl or C$_5$-C$_6$ cycloalkenyl group, phenyl, substituted C$_1$-C$_5$ alkyl wherein the substituents independently are 1 to 3 of C$_1$-C$_3$ alkyl; or R$_3$ is hydroxy, hydroximino or —O—C$_1$-C$_2$ alkyl-hydroximino;

R$_4$ is hydrogen, halogen, hydroxy, C$_1$-C$_2$-alkanoyloxy, (C$_1$-C$_3$ alkoxy)$_n$ where n is 1-2,

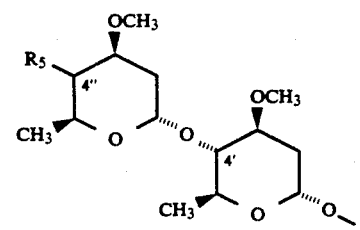

or

-continued

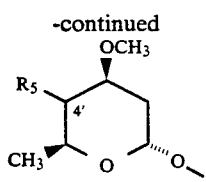

where $R_5$ is hydroxy, $C_1$-$C_2$ alkyl amino, $C_1$-$C_2$ alkanoyl amino, ($C_1$-$C_2$ alkyl)($C_1$-$C_2$ alkanoyl) amino, $C_1$-$C_2$ alkyl-S(O)$_m$, hydroxy substituted $C_1$-$C_2$ alkyl S(O)$_m$, where m is 0, 1 or 2.

4. A compound of claim 1 which is:
23-nor-23-thia-24-desmethyl-25-des(2-butyl) ivermectin B1;
23-nor-23-thia-24-desmethyl-25-des(2-butyl)-25-methyl ivermectin B1;
23-nor-23-thia-24-desmethyl-25-des(2-butyl)-25-ethyl ivermectin B1;
23-nor-23-thia-24-desmethyl-25-des(2-butyl)-25-isopropyl ivermectin B1;
23-nor-23-thia-24-desmethyl-25-des(2-butyl)-25-tert-butyl ivermectin B1;
23-nor-23-thia-24-desmethyl-25-des(2-butyl)-25-sec-butyl ivermectin B1;
23-nor-23-thia-24-desmethyl-25-des(2-butyl)-25-[2-(4-methylpent-2-enyl)] ivermectin B1;
23-nor-23-thia-24-desmethyl-25-des(2-butyl)-25-cyclohexyl ivermectin B1;
23-nor-23-thia-24-desmethyl-25-des(2-butyl)-25-phenyl ivermectin B1;
23-nor-23-thia-24-desmethyl-25-des(2-butyl)-25-(4-fluoro)phenyl ivermectin B1;
23-nor-23-thia-24-desmethyl-25-des(2-butyl)-25-(4-methoxy)phenyl ivermectin B1;
23-nor-23-sulfinyl-24-desmethyl-25-des(2-butyl) ivermectin B1;
23-nor-23-sulfinyl-24-desmethyl-25-des(2-butyl)-25-methyl ivermectin B1;
23-nor-23-sulfinyl-24-desmethyl-25-des(2-butyl)-25-isopropyl ivermectin B1;
23-nor-23-sulfinyl-24-desmethyl-25-des(2-butyl)-25-tert-butyl ivermectin B1;
23-nor-23-sulfinyl-24-desmethyl-25-des(2-butyl)-25-cyclohexyl ivermectin B1;
23-nor-23-sulfinyl-24-desmethyl-25-des(2butyl)-25-sec-butyl ivermectin B1;
23-nor-23-sulfinyl-24-desmethyl-25-des(2-butyl)-25-ethyl ivermectin B1;
23-nor-23-sulfinyl-24-desmethyl-25-des(2-butyl)-25-[2-(4-methylpent-2-enyl)] ivermectin B1;
23-nor-23-sulfinyl-24-desmethyl-25-des(2-butyl)-25-phenyl ivermectin B1;
23-nor-23-sulfonyl-24-desmethyl-25-des(2-butyl) ivermectin B1;
23-nor-23-sulfonyl-24-desmethyl-25-des(2-butyl)-25-methyl ivermectin B1;
23-nor-23-sulfonyl-24-desmethyl-25-des(2-butyl)-25-isopropyl ivermectin B1;
23-nor-23-sulfonyl-24-desmethyl-25-des(2-butyl)-25-tert-butyl ivermectin B1;
23-nor-23-sulfonyl-24-desmethyl-25-des(2-butyl)-25-cyclohexyl ivermectin B1;
23-nor-23-sulfonyl-24-desmethyl-25-des(2-butyl)-25-sec-butyl ivermectin B1;
23-nor-23-sulfonyl-24-desmethyl-25-des(2-butyl)-25-ethyl ivermectin B1;
23-nor-23-sulfonyl-24-desmethyl-25-des(2-butyl)-25-[2-(4-methylpent-2-enyl)] ivermectin B1;
23-nor-23-sulfonyl-24-desmethyl-25-des(2-butyl)-25-phenyl ivermectin B1;
23-nor-23-sulfonyl-24-desmethyl-25-des(2-butyl)-25-(4-fluoro)phenyl ivermectin B1;
23-nor-23-thia-24-desmethyl-25-des(2-butyl)-4''-deoxy-4''-epi-amino-25-isopropyl ivermectin B1;
23-nor-23-sulfonyl-24-desmethyl-25-des(2-butyl)-4''-deoxy-4''-epi-acetylamino-25-tert-butyl ivermectin B1;
23-nor-23-sulfinyl-24-desmethyl-25-des(2-butyl)-4''-deoxy-4''-epi-acetyl(methyl)amino-25-cyclohexyl ivermectin B1;
23-nor-23-thia-24-desmethyl-25-des(2-butyl)-5-deoxy-5-ketoxime-25-sec-butyl ivermectin B1;
23-nor-23-sulfonyl-24-desmethyl-25-des(2-butyl)-25-ethyl ivermectin B1 monosaccharide;
23-nor-23-thia-24-desmethyl-25-des(2-butyl)-25-[2-(4-methylpent-2-enyl)] ivermectin B1 aglycone;
23-nor-23-sulfonyl-24-desmethyl-25-des(2-butyl)-13-O-methoxymethyl-25-phenyl ivermectin B1 aglycone;
23-nor-23-sulfinyl-24-desmethyl-25-des(2-butyl)-13-deoxy-13-fluoro-25-(4-fluoro)phenyl ivermectin B1;
23-nor-23-thia-24-desmethyl-25-des(2-butyl)-13-O-methoxyethoxymethyl-25-isopropyl ivermectin B1 aglycone;
23-nor-23-sulfonyl-24-desmethyl-25-des(2-butyl)-13-deoxy-13-chloro-25-tert-butyl ivermectin B1 aglycone;
23-nor-23-thia-24-desmethyl-25-des(2-butyl)-13-deoxy-25-cyclohexyl ivermectin B1 aglycone;
23-nor-23-sulfonyl-24-desmethyl-25-des(2-butyl)-4''-deoxy-4''-epi-(2-acetylaminoethyl)thio-25-sec-butyl ivermectin B1;
23-nor-23-sulfonyl-24-desmethyl-25-des(2-butyl)-4''-deoxy-4''-epi-(2-acetylaminoethyl)sulfonyl-25-tert-butyl ivermectin B1.

5. A composition useful for the treatment of parasitic infections in animals or parasitic infestations of plants which comprises an inert carrier and a compound of claim 1.

6. A method for the treatment of parasitic infections of animal which comprises administering to an animal infected with such parasites a compound of claim 1.

7. A method for the treatment of parasitic infestations of plants which comprises applying to such plant or the soil in which it grows, an effective amount of a compound of claim 1.

8. A method for the treatment of premises infected with parasites which comprises applying to such premises an effective amount of a compound of claim 1.

* * * * *